United States Patent [19]

Kummer et al.

[11] Patent Number: 4,931,590

[45] Date of Patent: Jun. 5, 1990

[54] PREPARATION OF ADIPIC ACID

[75] Inventors: Rudolf Kummer; Franz Merger, both of Frankenthal; Werner Bertleff, Viernheim; Rolf Fischer, Heidelberg, all of Fed. Rep. of Germany

[73] Assignee: BASF Aktiengesellschaft, Ludwigshafen, Fed. Rep. of Germany

[21] Appl. No.: 205,340

[22] Filed: Jun. 10, 1988

[30] Foreign Application Priority Data

Jun. 15, 1987 [DE] Fed. Rep. of Germany ....... 3719936

[51] Int. Cl.$^5$ ..................... C07C 55/14; C07C 27/02
[52] U.S. Cl. ..................... 562/590; 560/177; 560/190; 560/210; 560/266; 562/593
[58] Field of Search ................ 562/590; 560/177, 210, 560/190, 211

[56] References Cited

U.S. PATENT DOCUMENTS

| | | | |
|---|---|---|---|
| 3,941,851 | 3/1976 | Smith | 560/238 |
| 4,517,400 | 5/1985 | Pesa et al. | 585/638 |
| 4,537,987 | 8/1985 | Schneider et al. | 560/193 |
| 4,801,738 | 1/1989 | Schneider et al. | 560/177 |

FOREIGN PATENT DOCUMENTS

| | | | |
|---|---|---|---|
| 56489 | 7/1982 | European Pat. Off. | 562/590 |
| 0081090 | 6/1983 | European Pat. Off. | |
| 0131860 | 1/1985 | European Pat. Off. | |
| 0125567 | 1/1986 | European Pat. Off. | |
| 3317164 | 11/1984 | Fed. Rep. of Germany | 560/177 |

Primary Examiner—Vivian Garner
Attorney, Agent, or Firm—Keil & Weinkauf

[57] ABSTRACT

Adipic acid is prepared by a process which comprises the following steps:

(a) Hydroformylation of a pentenoic ester by reaction with carbon monoxide and hydrogen at elevated temperatures and under superatmospheric pressure in the presence of a cobalt carbonyl or rhodium carbonyl complex with formation of a mixture of 5-, 4- and 3-formylvaleric esters, (b) isolation of the 5-formylvaleric ester from the resulting mixture of 5-, 4- and 3-formylvaleric esters, a mixture essentially consisting of 4- and 3-formylvaleric esters remaining, (c) dehydrocarbonylation of the mixture consisting essentially of 4- and 3-formylvaleric esters in the presence of one or more elements of subgroup 8 of the Periodic Table at from 50° to 400° C. with formation of pentenoic esters, and recycling of the latter to stage (a) for hydroformylation, (d) oxidation of the 5-formylvaleric ester from stage (b) with molecular oxygen or a gas containing molecular oxygen to give a monoester of adipic acid, and (e) hydrolysis of the monoester of adipic acid to give adipic acid.

13 Claims, No Drawings

PREPARATION OF ADIPIC ACID

In the preparation of adipic acid by hydroesterification of pentenoic esters, substantial amounts of 2-methylglutaric esters and 3-ethylsuccinic esters are obtained as byproducts. Thus, adipic acid is obtained only from a fraction of the pentenoic esters used.

European Patent No. 131,860 discloses that pentenoic esters can be hydroformylated in the presence of cobalt carbonyl or rhodium carbonyl complexes, and the resulting 5-formylvaleric esters can be oxidized with molecular oxygen to give monoesters of adipic acid. In this process too, the selectivity with respect to 5-formylvaleric esters is 71.8%, so that substantial amounts of byproducts have to be accepted.

Attempts have already been made first to isomerize 3-pentenoic esters catalytically to 4-pentenoic esters and then to subject the latter to hydroformylation to give formylvaleric esters, as disclosed in European Patent No. 125,567. In this process too, it is not possible to reduce the proportion of isomeric formylvaleric esters to an industrially acceptable level.

Furthermore, U.S. Pat. No. 4,517,400 discloses that aldehydes can be dehydrocarbonylated in the presence of zeolites which contain catalytically active metals to give the corresponding starting olefins. However, when a mixture of n- and isobutyraldehyde is heated to 300° C. in the presence of such catalysts, only n-butyraldehyde is decarbonylated to propylene whereas isobutyraldehyde is not attacked. Application of this reaction to formylvaleric esters did not appear appropriate since, according to European Patent Application No. 81,090, formylbutyric esters undergo cyclization to give dihydropyrones, and a similar cyclization of the isomeric formylvaleric esters was expected.

It is an object of the present invention to provide a process for the preparation of adipic acid starting from pentenoic esters, in which the pentenoic ester is converted as completely as possible into adipic acid, additional isomerization of pentenoic esters to 4-pentenoic esters is not necessary and, finally, the production of useless branched isomers and further byproducts is reduced.

We have found that this object is achieved by a process for the preparation of adipic acid which comprises the following steps:

(a) Hydroformylation of a pentenoic ester by reaction with carbon monoxide and hydrogen at elevated temperatures and under superatmospheric pressure in the presence of a cobalt carbonyl or rhodium carbonyl complex with formation of a mixture of 5-, 4- and 3-formylvaleric esters, (b) isolation of the 5-formylvaleric ester from the resulting mixture of 5-, 4- and 3-formylvaleric esters, a mixture essentially consisting of 4- and 3-formylvaleric esters remaining, (c) dehydrocarbonylation of the mixture consisting essentially of 4- and 3-formylvaleric esters in the presence of one or more elements of subgroup 8 of the Periodic Table at from 50° to 400° C. with formation of pentenoic esters, and recycling of the latter to stage (a) for hydroformylation, (d) oxidation of the 5-formylvaleric ester from stage (b) with molecular oxygen or a gas containing molecular oxygen to give a monoester of adipic acid, and (e) hydrolysis of the monoester of adipic acid to give adipic acid.

The novel process has the advantage that adipic acid is obtained starting from pentenoic esters, while avoiding undesirable isomers. Another advantage of the novel process is that the production of other byproducts and cyclic compounds is minimized.

In stage (a), pentenoic esters are hydroformylated. Suitable pentenoic esters are derived from alkanols of 1 to 12 carbon atoms or cycloalkanols of 5 to 8 carbon atoms. $C_1$–$C_{12}$-alkyl pentenoates, in particular $C_1$–$C_4$-alkyl pentenoates, e.g. methyl pentenoate, are particularly preferred. Examples of suitable compounds are 4-pentenoic esters, 3-pentenoic esters and 2-pentenoic esters, individually or as mixtures with one another. Examples are methyl, ethyl, propyl, isopropyl, butyl, hexyl, nonyl, dodecyl, cyclopentyl and cyclohexyl esters of 2-, 3- and 4-pentenoic acid.

The hydroformylation of the pentenoic esters is carried out at elevated temperatures, advantageously at from 60° to 160° C., in particular from 80° to 120° C., under superatmospheric pressure, advantageously from 5 to 300 bar. The said hydroformylation is effected by reaction with carbon monoxide and hydrogen. As a rule, the gas mixture contains carbon monoxide and hydrogen in a molar ratio of from 1:0.5 to 1:10, in particular from 1:1 to 1:2.

The hydroformylation is carried out in the pressence of a cobalt carbonyl or rhodium carbonyl complex. The carbonyl complexes can be prepared before the reaction from cobalt or rhodium salts by reaction with carbon monoxide. Advantageously, they are formed in situ from the salts of rhodium or of cobalt. The cobalt carbonyl or rhodium carbonyl complexes used are preferably additionally modified by tertiary phosphines or tertiary phosphites. Suitable phosphines or phosphites have alkyl radicals of not more than 12 carbon atoms and/or phenyl radicals which may additionally contain alkyl groups of not more than 4 carbon atoms as substituents. Triphenylphosphine, substituted triarylphosphines, such as tritolylphosphine, and alkyldiarylphosphines, such as hexyldiphenylphosphine, are preferably used.

If cobalt carbonyl camplexes are used, it has proven useful if from 0.01 to 1, preferably from 0.05 to 0.3, in particular from 0.08 to 0.25, mol %, calculated as cobalt and based on pentenoic esters used, of a cobalt carbonyl complex is employed. In addition, it is advantageous to maintain the conversion of the pentenoic esters used at 10–50%, in particular 20–40%. This reduces the formation of byproducts by hydrogenation and aldolization. Under these conditions, it is possible to dispense with the presence of solvents and to use cobalt carbonyl complexes which contain up to 20 moles of tertiary nitrogen bases per mole of cobalt without adversely affecting the hydroformylation. Such catalysts are obtained, for example, in the hydroesterification of butadiene to pentenoic esters, as described in European Patent No. 31,100.

If rhodium carbonyl complexes are used, a temperature of from 100° to 120° C. and a pressure of from 5 to 20 bar are advantageously maintained. The concentration of rhodium carbonyl complexes is advantageously from 5 to 500 ppm, calculated as metal and based on the reaction mixture. Modification of the rhodium carbonyl complexes with the abovementioned phosphines or phosphites has proven particularly useful. Advantageously, phosphines or phosphites are used in a 3-fold to 100-fold molar excess, based on rhodium.

It is also possible to carry out the hydroformylation in the presence of solvents which are inert under the reaction conditions. Examples of suitable solvents are ethers, such as tetrahydrofuran, carboxylic esters, such as valeric esters, butyric esters or acetic esters, and hydrocarbons, such as toluene.

Advantageously, the hydroformylation mixture is let down and then worked up by a conventional method. A suitable method for working up reaction mixtures containing cobalt carbonyl complexes is described in, for example, European Patent No. 31,100. In this procedure, the mixture discharged from the hydroformylation reaction is let down and then treated with an oxidizing agent, such as hydrogen peroxide or a gas containing molecular oxygen, in particular air, advantageously in an amount of from 2 to 10 oxidation equivalents per mole of cobalt catalyst, in the presence of an aqueous solution, for example aqueous formic acid or acetic acid, butyric acid, valeric acid or 2-ethylhexanoic acid, at, for example, from 80° to 160° C., in particular from 100° to 130° C. Depending on the degree of mixing, the cobalt catalyst has separated off completely after only a few seconds or fractions of a second. The coblt-containing aqueous phase is advantageously separated off by decanting. The organic phase obtained is a mixture of 5-, 4- and 3-formylvaleric esters which also contains high boilers and valeric esters as byproducts, as well as unconverted pentenoic esters and, where relevant, solvents.

The mixture of formylvaleric esters which has been freed from the catalyst is separated by distillation. As a rule, any solvent present and unconverted pentenoic esters are first separated off individually or as a mixture and are advantageously recycled to the hydroformylation stage. In stage (b), the 5-formylvaleric ester is isolated by distillation from the resulting mixture, which contains 5-, 4- and 3-formylvaleric esters and may contain small amounts of high boilers, the remaining mixture essentially consisting of 4- and 3-formylvaleric esters. Depending on the efficiency of the separation, small amounts, for example up to 5% by weight, of 5-formylvaleric esters may also be present.

In stage (c), the resulting mixture, which essentially consists of 4- and 3-formylvaleric esters, is then subjected to dehydrocarbonylation at from 50° to 400° C. in the presence of one or more elements of subgroup 8 of the Periodic Table, with formation of pentenoic esters, and the pentenoic esters obtained are recycled to stage (a) for hydroformylation.

Although the pure 4- and 3-formylvaleric esters can be used for the novel process, it is generally advantageous to use mixtures of these esters, which, depending on the efficiency of the distillation, may also contain 5-formylvaleric esters. A typical mixture contains, for example, from 60 to 75% by weight of 4-formylvaleric ester, from 25 to 35% by weight of 3-formylvaleric ester and up to 5% by weight of 5-formylvaleric ester. The dehydrocarbonylation products obtained are 4-, 3- and 2-pentenoic esters, predominantly the 3-pentenoic ester.

Suitable homogeneous catalysts are complexes of noble metals of subgroup 8 of the Periodic Table, in particular of ruthenium or rhodium. Ruthenium or rhodium complexes which contain halogens, such as chlorine or bromine and phosphines or phosphites and may additionally contain carbon monoxide as a ligand are particularly suitable. Particularly preferably used modifiers are tertiary organic phosphines or phosphites. Such phosphines or phosphites preferably have alkyl of not more than 18 carbon atoms, cycloalkyl of 5 to 12 carbon atoms, aralkyl of 7 to 10 carbon atoms or aryl of 6 to 10 carbon atoms, in particular phenyl, as substituents. The radicals may be identical or different. Examples of suitable complexes are $RhCl[P(C_6H_5)_3]_3$, $Ru_2Cl_3[(P(C_6H_5)(C_2H_5)_2)_6]Cl$, $RhBr(CO)[P(C_6H_5)_3]_2$, $HRuCl(CO)[P(C_6H_5)_2]_3$ and $RhCl(CO)[P(C_6H_5)_3]_2$.

Supported catalysts which contain one or more of the elements of subgroup 8 of the Periodic Table, such as palladium, platinum, ruthenium, rhodium, osmium, iridium, iron, cobalt or nickel, in particular noble metals of this group, are preferred. Other advantageous supported catalysts are those which contain two or more noble metals of subgroup 8 of the Periodic Table, such as ruthenium, rhodium, palladium or platinum. Other preferred catalysts contain one or more of the above-mentioned noble metals of subgroup 8 of the Periodic Table and additionally one or more metals selected from the group consisting of iron, cobalt and nickel.

The supported catalysts advantageously contain from 0.01 to 10, preferably from 0.05 to 5, in particular from 0.05 to 1, % by weight, based on the sum of the carrier and catalytically active metals and calculated as metals, of active metals of subgroup 8 of the Periodic Table. Advantageously used carriers are alumina, silica, titanium dioxide, zirconium dioxide, zinc oxide, lanthanum oxide, barium sulfate or mixtures of these oxides, as well as aluminum silicates.

The state supported catalysts particularly advantageously also contain one or more elements of subgroups 1 to 7 of the Periodic Table and/or rare earth elements, such as zinc, copper, silver, lanthanum, titanium, vanadium, chromium, molybdenum, tungsten, manganese, rhenium, cerium, neodymium or praseodymium, advantageously in an amount of from 0.05 to 2% by weight, based on the total weight of the catalyst (carrier and catalytically active metals) and calculated as metal.

For example, impregnated catalysts in which the catalytically active metals are concentrated at the surface of the carrier have proven useful. Catalysts of this type are obtained in a conventional manner by impregnating preshaped carriers, such as pellets, spheres or extrudates, with an aqueous solution of the metal salts, which are converted into their oxides on heating, for example the nitrates, and the products can then be dried, calcined and used directly or, if necessary, after reduction with hydrogen or another reducing agent.

The catalysts used in stage (c) possess high activity over a fairly long period. Spent catalysts can be regenerated by treatment with an oxygen-containing gas, for example air, at from 350° to 500° C. and, if necessary, subsequent reduction.

In the dehydrocarbonylation in stage (c), a temperature of from 60° to 350° C., in particular from 100° to 280° C., preferably from 120° to 200° C., is advantageously maintained. In general, the cleavage is carried out under atmospheric pressure, although it is also possible to use reduced or superatmospheric pressure, advantageously from 10 mbar to 20 bar. In general, a space velocity of from 0.01 to 40, preferably from 0.1 to 20, kg of formylvaleric ester per kg of catalyst per hour is maintained.

The dehydrocarbonylation in stage (c) is advantageously carried out in the presence of molecular oxygen or a gas which contains molecular oxygen and an inert gas, such as nitrogen, carbon dioxide, argon or steam, for example air. A molar ratio of formylvaleric esters to molecular oxygen of from 1:0.05 to 1:3, in particular from 1:0.2 to 1:1.5, e.g. from 1:0.25 to 1:1.25, is preferably used. This increases the catalyst life and in particular the yield of pentenoic esters. The presence of molecular oxygen was not indicated since methyl 5-formylvalerate is oxidized by molecular oxygen to monomethyl adipate in a yield of 96% at as low as 50° C., as disclosed in European Patent No. 131,860 mentioned at the outset, and it was therefore to be expected that 4- and 3-formylvaleric esters would be oxidized to monoesters of 2-methylglutaric acid and of 3-ethylsuccinic acid in a similar manner.

It may be advantageous to carry out the dehydrocarbonylation of the formylvaleric esters in stage (c) with the additional use of diluents. Examples of suitable diluents are water, alcohols, such as methanol, ethanol, butanol or cyclohexanol, ethers, such as dioxane or tetrahydrofuran, and chlorohydrocarbons, such as methylene chloride, chloroform or 1,2-dichloromethane, as well as aliphatic, cycloaliphatic or aromatic hydrocarbons, such as benzene, toluene, cyclohexane or paraffins, and esters, such as acetates or propionates. The alcohol corresponding to the alcohol of the formylvaleric esters is advantageously used. Thus, the educt and product have sufficiently different boiling points and can therefore be readily separated by distillation. It has proven useful if the molar ratio of formylvaleric esters to diluents is from 1:0.1 to 1:50, in particular from 1:0.5 to 1:20. Particularly preferred diluents are water and alkanols of 1 to 6 carbon atoms, in particular methanol.

The dehydrocarbonylation in stage (c) can be carried out batchwise or continuously as a fixed-bed reaction using fixed-bed catalysts, for example by the liquid phase or trickle-bed method in the liquid or gas phase, or as a fluidized-bed reaction with catalysts fluidized upward and downward, in the gas phase, or in the liquid phase with soluble catalysts or suspended supported catalysts.

A preferred embodiment of stage (c) in the liquid phase is carried out, for example, as follows: the formylvaleric ester and, if required, a diluent are passed together with an oxygen-containing gas at below the boiling point of the formylvaleric ester over a solid catalyst or are heated in the presence of a suspended solid catalyst or of a dissolved homogeneous catalyst. After removal of the catalyst, the resulting liquid reaction product is then separated into pentenoic esters and, where relevant, diluent and unconverted formylvaleric esters by distillation.

Another preferred embodiment of stage (c) in the gas phase is carried out, for example, as follows: a mixture of formylvaleric esters and, if required, a diluent is vaporized and is then passed, together with air, advantageously with an additional carrier gas, such as nitrogen, carbon dioxide or argon, at the stated temperature and in gaseous form, into a fixed-bed or fluidized-bed catalyst. The reacted mixture is condensed and then separated by fractional distillation. Unconverted formylvaleric esters are advantageously recycled to stage (c). The resulting mixture of 4-, 3- and 2-pentenoic esters is recycled to the hydroformylation stage (a), if appropriate together with pentenoic esters obtained in stage (b). The valeric esters obtained as byproducts can be separated off or likewise recycled as a solvent to stage (a).

In stage (d), the 5-formylvaleric esters obtained in stage (b) are oxidized with molecular oxygen or a gas containing molecular oxygen to give monoesters of adipic acid. The oxidation is advantageously carried out at from 20° to 100° C., in particular from 50° to 97° C., and under from 1 to 10 bar. The gas containing molecular oxygen may contain, for example, up to 80% by volume of inert gases, such as nitrogen, carbon dioxide or noble gases. The oxidation generally takes place in the absence of a catalyst. It can, however, be further accelerated by the addition of catalysts, such as alkali metal hydroxides, e.g. potassium hydroxide or sodium hydroxide, in amounts of from 0.001 to 0.5% by weight, or metal salts of cobalt or manganese, for example cobalt acetate or manganese acetate, in amounts of from 0.001 to 0.1, preferably from 0.02 to 0.08, % by weight, calculated as metal. Advantageously, pure monoesters of adipic acid are obtained from the reaction mixture by distillation.

In stage (e), the resulting monesters of adipic acid are hydrolyzed to adipic acid. From 1 to 200, in particular from 50 to 150, moles of water are advantageously used per mole of monoester of adipic acid. Solvents which are inert under the reaction conditions may also be present. Examples of suitable solvents are hydrocarbons, such as cyclohexane or toluene, halohydrocarbons, such as dichloromethane or tetrachloromethane, and ethers, such as dioxane or diglyme. If solvents are present, the monoester of adipic acid is used in the form of a 1–90, in particular 5–20, % strength by weight solution, advantageously as an aqueous solution.

The hydrolysis is expediently carried out at from 30° to 200° C., advantageously from 50° to 200° C., in general under atmospheric pressure, although it is also possible to use slightly reduced or slightly superatmospheric pressure, for example up to 20 bar.

The hydrolysis is advantageously carried out in the presence of acidic media. Examples of suitable acidic media are sulfonic acids, such as p-toluenesulfonic acid, Lewis acids, such as zinc chloride, non-oxidizing mineral acids, such as sulfuric acid, hydrochloric acid or hydrobromic acid, lower fatty acids, i.e. lower aliphatic carboxylic acids, such as formic acid, acetic acid or propionic acid, and oxalic acid, and strongly acidic cation exchangers which, for example, are composed of crosslinked polystyrene containing sulfo groups or phenol resins possessing sulfo groups or phenol resins possessing sulfo groups, as well as acidic zeolites.

Acids are advantageously used for the hydrolysis in the homogeneous phase in catalytic amounts, for example from 0.002 to 0.25 mole per mole of monoester of adipic acid. Aliphatic carboxylic acids are generally used in amounts of from 0.1 to 1 mole per mole of monoester of adipic acid. Strongly acidic cation exchangers are particularly preferably used.

The process may be carried out batchwise or, advantageously, continuously, for example in a cascade of stirred kettles. In this procedure, it is advantageous if the alcohol obtained during the hydrolysis is separated off continuously from the reaction mixture by distillation. Where strongly acidic cation exchangers are used, it is advantageous to carry out the reaction in such a way that the strongly acidic cation exchanger is arranged as a fixed bed in, for example, a tube reactor and the reaction mixture is passed over the said cation exchanger by the trickle-bed method. In a particularly advantageous embodiment, the reaction mixture is first passed by the trickle-bed procedure through a first reaction zone containing strongly acidic cation exchangers in a fixed bed and then, in a second reaction zone, circulated over strongly acidic cation exchangers in a fixed bed, and the reaction mixture is removed at the rate at which it is fed to the first zone.

In another advantageous procedure, the monoester of adipic acid and water in excess are passed through a column charged with strongly acidic cation exchangers, the alcohol is distilled off at the upper end and an aqueous solution of adipic acid is taken off at the other end. Adipic acid can be obtained in pure form from the resulting aqueous solution by crystallization.

Adipic acid obtainable by th process according to the invention is an important starting material for the preparation of polyamides.

The Example which follows illustrates the process according to the invention.

EXAMPLE (a) The hydroformylation experiments were carried out in a continuously operated apparatus. This possessed a liquid metering pump, by means of which the methyl pentenoate and the dissolved cobalt catalyst were conveyed into the two stirred autoclaves connected in series. The synthesis gas was combined with the liquid feed upstream of the first reactor, the pressure being regulated. The two reactors had liquid volumes of 1.2 and 1.12 l, respectively. The two-phase mixture discharged was collected under pressure in a container, from which a certain amount of waste gas was discharged via a pressure regulating valve. The liquid phase was let down into a receiver, the level being regulated.

In this apparatus, a mixture of methyl 3-pentenoate was subjected to hydroformylation using 800 ppm of cobalt in the form of $Co_2(CO)_8$ (360 ml/h) at 100° C. and under 130 bar ($CO/H_2=1:1$). 327 g/h of mixture were discharged, the mixture having the following composition:

38.1% (m/m) of methyl formylvalerate (containing 69.6% of n component),
0.4% (m/m) of methyl valerate and
61.2% (m/m) of methyl pentenoate.

This result corresponds to a conversion of 33%, a selectivity of 98.8%, based on total formylvaleric esters, and a selectivity of 68.8%, based on 5-formylvaleric ester.

This discharged mixture was passed together with 150 ml/hour of 5% strength acetic acid through a tube, 5 l/hour of air being passed in and thorough mixing being effected. After phase separation, 154 ml of a 0.2% strength cobalt acetate solution (calculated as cobalt) was separated off.

(b) In a batchwise distillation, 835 g of the organic phase were separated into about 3 g of methyl valerate, 495 g of methyl 3-pentenoate, 12 g of methyl 2-transpentenoate and about 315 g of a mixture of methyl 5-, 4-and 3-formylvalerate, and 6 g of residue.

The mixture of methyl formylvalerates was separated by further fractional distillation into 215 g of methyl 5-formylvalerate (99% pure), 90 g of a mixture of methyl 5-, 4- and 3-formylvalerate (2% of 5-, 70% of 4- and 28% of 3-formylvalerate) and 10 g of residue.

(c) In the course of 1 hour, the mixture of 90 g of methyl 5-, 4- and 3-formylvalerates from stage (b) was pumped together with 180 g of methanol into an evaporator and passed from there, together with 70 l of air, at 250° C., over 200 g of an $SiO_2$ supported catalyst which contained 0.5% by weight of Ru, 0.5% by weight of Rh and 0.5% by weight of Pt. When the condensed reacted mixtures (260 g) were worked up by distillation, 53 g of pentenoic esters and valeric esters (15% of methyl 4-pentenoate, 53% of methyl 3-pentenoate and 15% of methyl 2-transpentenoate and 17% of methyl valerate) were obtained after removal of methanol and water. Furthermore, 10 g of a mixture of methyl 4-formylvalerate and methyl 3-formylvalerate were recovered. The mixture of methyl 4-pentenoate, methyl 3-pentenoate and methyl 2-pentenoate was hydroformylated to formylvaleric esters in the presence of the methyl valerate in stage (a), once again with virtually the same yield as that obtained starting from methyl 3-pentenoate.

(d) 215 g of the methyl 5-formylvalerate obtained in stage (b) were introduced into a bubble column and gassed with 8 l/hour of oxygen for 5.5 hours at $55\pm2°$ C. under atmospheric pressure. After this reaction time, the conversion was quantitative. 225 g (95% yield) of monomethyl adipate of boiling point 113° C./0.6 mbar were obtained from the oxidation product by fractional distillation.

(e) 16 g of a strongly acidic ion exchanger (crosslinked polystyrene containing sulfo groups) were suspended in a solution of 160 g of monomethyl adipate prepared according to (c), in 270 g of water. The reaction mixture was heated in a 1 l three-necked flask with an attached spinning band column until no further methanol passed over. The ion exchanger was filtered off; 144.5 g (99% yield) of adipic acid of melting point 153° C. were obtained from the filtrate after crystallization and partial evaporation of the mother liquor.

We claim:

1. A process for the preparation of adipic acid which comprises the following steps:
   (a) hydroformylation of a pentenoic ester by reaction with carbon monoxide and hydrogen at elevated temperatures and under superatmospheric pressure in the presence of a cobalt carbonyl or rhodium carbonyl complex with formation of a mixture of 5-, 4- and 3-formylvaleric esters,
   (b) isolation of the 5-formylvaleric ester from the resulting mixture of 5-, 4- and 3-formylvaleric esters, a mixture essentially consisting of 4- and 3-formylvaleric esters remaining,
   (c) dehydrocarbonylation of the mixture consisting essentially of 4- and 3-formylvaleric esters in the presence of one or more elements of subgroup 8 of the Periodic Table at from 50° to 400° C. with formation of pentenoic esters, and recycling of the latter to stage (a) for hydroformylation,
   (d) oxidation of the 5-formylvaleric ester from stage (b) with molecular oxygen or a gas containing molecular oxygen to give a monoester of adipic acid, and
   (e) hydrolysis of the monoester of adipic acid to give adipic acid.

2. The process of claim 1, wherein, in stage (a), a cobalt concentration of from 0.05 to 0.3 mol %, based on pentenoic esters, is maintanined.

3. The process of claim 1, wherein, in stage (a), a conversion of pentenoic esters of from 10 to 50% is maintained.

4. The process of claim 1, wherein, in stage (a), a temperature of from 60° to 160° C. is maintained.

5. The process of claim 1, wherein, in stage (c), a supported catalyst is used which contains from 0.01 to 10% by weight of one or more metals of sub-group 8 of the Peridic Table.

6. The process of claim 1, wherein a supported catalyst is used which contains two or more noble metals of subgroup 8 of the Periodic Table.

7. The process of claim 1, wherein a supported catalyst is used which contains one or more noble metals of subgroup 8 of the Periodic Table and one or more metals selected from the group consisting of iron, cobalt and nickel.

8. The process of claim 1, wherein, in stage (c), a supported catalyst is used which contains one or more metals of subgroup 8 of the Periodic Table and in addition one or more of the elements copper, silver, zinc, titanium, vanadium, chromium, molybdenum, tungsten, manganese and rhenium.

9. The process of claim 1, wherein, in stage (c), a temperature of from 60° to 350° C. is maintained.

10. The process of claim 1, wherein, in stage (c), molecular oxygen or a gas containing molecular oxygen is concomitantly used.

11. The process of claim 1, wherein a molar ratio of formylvaleric esters to molecular oxygen of from 1:0.05 to 1:3 is maintained.

12. The process of claim 1, wherein, in stage (c), a diluent is concomitantly used.

13. The process of claim 1, wherein the reaction in stage (c) is carried out in the presence of water or of an alkanol of 1 to 6 carbon atoms or of a mixture of these.

* * * * *

UNITED STATES PATENT AND TRADEMARK OFFICE
CERTIFICATE OF CORRECTION

PATENT NO. : 4,931,590
DATED : June 5, 1990
INVENTOR(S) : Rudolf KUMMER et al.

It is certified that error appears in the above-identified patent and that said Letters Patent is hereby corrected as shown below:

Column 8, line 50

"the Periodic table at from 50 to 400°C. with" should read --the Periodic Table and optionally, one or more of the elements copper, silver, zinc, titanium, vanadium, chromium, molybdenum, tungsten, manganese, and rhenium, at from 50 to 400°C. optionally, in the presence of molecular oxygen or a gas containing molecular oxygen and optionally, in the presence of a diluent with--

Column 9, line 3, 6, Column 10, line 8
"wherein" should read --wherein in stage c)--

Signed and Sealed this

Thirteenth Day of August, 1991

Attest:

HARRY F. MANBECK, JR.

Attesting Officer

Commissioner of Patents and Trademarks